United States Patent

Garlick et al.

[11] 3,992,571
[45] Nov. 16, 1976

[54] DIFFERENTIAL OPTICAL POLARISATION DETECTORS

[75] Inventors: George Frederick John Garlick, Market Weighton; Gottfried Albert Steigmann, Cottingham; William Edward Lamb, Little Weighton, all of England

[73] Assignee: National Research Development Corporation, London, England

[22] Filed: May 9, 1974

[21] Appl. No.: 468,584

[30] Foreign Application Priority Data

May 11, 1973 United Kingdom............... 22586/73
Mar. 20, 1974 United Kingdom............... 12361/74

[52] U.S. Cl............................. 178/6; 178/DIG. 31; 178/DIG. 34; 178/DIG. 37; 178/6.5; 356/114; 350/14; 350/132
[51] Int. Cl.$^2$........................................... H04N 7/02
[58] Field of Search............... 178/6.5, 6, DIG. 31, 178/DIG. 34, DIG. 37, DIG. 1; 350/14, 15, 132, 133; 356/114, 115, 116; 324/77 K; 250/225

[56] References Cited
UNITED STATES PATENTS

| 3,317,662 | 5/1967 | Robinson............................. 178/5.4 |
| 3,700,334 | 10/1974 | Low et al............................ 356/106 |
| 3,864,513 | 2/1975 | Halojian............................ 178/6.6 R |

FOREIGN PATENTS OR APPLICATIONS

| 1,149,064 | 7/1967 | United Kingdom..................... 178/6 |

*Primary Examiner*—Benedict V. Safourek
*Assistant Examiner*—Edward L. Coles
*Attorney, Agent, or Firm*—Cushman, Darby & Cushman

[57] ABSTRACT

A detector for differential optical polarisation effects comprises a television camera incorporating a polarisation analysing system, the camera generating two similar video signals representing two views of the same scene which are derived by means of light components differing only in respect of their polarisation characteristics. The two video signals are compared over the whole scene on a point-by-point basis, the result of the comparison suitably being displayed in pictorial form.

4 Claims, 3 Drawing Figures

DIFFERENTIAL OPTICAL POLARISATION DETECTORS

When unpolarised light is reflected, either specularly or diffusely, from various kinds of surface it becomes partially polarised. The degree of polarisation of the reflected light is a strong function of the angles of incidence and reflection at the surface and may vary across the surface due to changes in the surface structure or to contaminations and impressions on the surface. In the case of light reflected from a layer of dust the degree of polarisation can change markedly if the layer is in motion or is fluidised. While standard techniques of polarimetric analysis can be employed to study such variations in polarisation, it would be useful for various purposes to have a means whereby differential effects over a given area of surface could readily be detected and, if desired, displayed in pictorial form. Examples of such purposes are the inspection of crops in order to locate foci of disease at earlier stages than can be detected by discoloration or in order to study the effects of treatment with herbicides etc., the inspection of soil surfaces in order to locate disturbed areas corresponding to buried objects, the examination of small surface areas for features such as finger prints and stains, and the detection of local dust disturbances on lunar or planetary surfaces.

Accordingly, the present invention provides a differential optical polarisation detector comprising a television camera operative to generate two similar video signals respectively representing two views of the same scene, the camera incorporating a polarisation analysing system arranged so that said two views are respectively derived by means of components of the light from the scene which differ only in respect of their polarisation characteristics, and means for comparing the two video signals over the whole scene on a point-by-point basis.

It is to be understood that in this specification the term light includes ultra-violet and infra-red radiation as well as visible radiation.

The two video signals may be generated simultaneously, being derived in the same manner respectively by means of two separate photosensitive screens in the camera; the two screens may be incorporated respectively in a pair of matched conventional camera tubes, or use may be made of a camera tube of a type incorporating two separate photosensitive screens such as that supplied by Radio Corporation of America under the name "Bivicon." Alternatively, the two video signals may be generated successively, being derived in the same manner by means of a single photosensitive screen in the camera and one signal being appropriately delayed with respect to the other before the comparison between them is made. In the latter case, care may be necessary in the use of the detector to avoid complications arising from very rapid temporal variations in the scene viewed by the camera.

In either case, the differential effects detected by comparison of the two video signals will of course depend on the relevant polarisation characteristics of the components of the light from the scene by means of which the two views are derived, and hence on the specific design of the polarisation analysing system incorporated in the camera. In the following description, attention will be confined to the case of linear polarisation, but it is to be understood that similar considerations can be applied to the detection of differential effects associated with circular or elliptical polarisation.

Thus, considering the case where the two video signals are generated simultaneously, the polarisation analysing system may suitably consist of two linear polarisers respectively disposed in front of the two photosensitive screens and having their polarising directions set at right angles to each other. Suppose that the camera views a scene such that the light reaching the camera from the scene is partially linearly polarised, and consider the intensities of illumination at a pair of corresponding points on the two sceens, which for convenience will be referred to as A and B. In the absence of the polarisers these intensities would have been equal (say of value I) with a fraction $p$ of the total intensity being due to the linearly polarised component. Denoting by $I_A$ and $I_B$ respectively the intensities of illumination at the relevant points on the screens A and B with the polarisers present, and assuming that there is negligible absorption of light in the polarisers, it can readily be shown that:

$$I_A + I_B = I,$$
$$I_A - I_B = pI\cos 2\theta,$$

and hence $$(I_A - I_B)/(I_A + I_B) = p\cos 2\theta,$$

where $\theta$ is the angle between the vibration plane of the linearly polarised component and the polarising direction of the polariser in front of the screen A. It may be noted here that in most cases the orientation of this vibration plane will be known in advance for a given application of the detector, so that the polarisers may be set to give a valve of zero for the angle $\theta$ and hence a value of unity for cos $2\theta$.

The video signals respectively derived by means of the screens A and B will of course provide representations of the respective spatial variations of $I_A$ and $I_B$; denoting by $V_A$ and $V_B$ the respective instantaneous magnitudes of these two signals after any necessary gamma correction, it will be seen that by deriving a composite video signal having an instantaneous magnitude proportional to $(V_A - V_B)/(V_A + V_B)$ one can obtain a representation of the spatial variations of the degree of polarisation defined by the quantity $(I_A - I_B)/(I_A + I_B)$. This composite video signal may be utilized to control the spatial variations of brightness in a picture displayed by a cathode ray tube, or may be utilised to control the spatial variations of colour in a picture displayed by a colour television tube. In the latter case it is preferred to use digitising techniques such that the picture provides a stepwise colour coding of the degree of polarisation; this enables better contrast appreciation to be achieved than is the case with a continuously graded monochrome or colour display. The composite video signal can also, or instead, be fed to a suitable data processing apparatus. A composite video signal of the form referred to is not affected by variations of brightness over the scene viewed by the camera, as would be the case with a simple difference signal having an instantaneous magnitude proportional to $(V_A - V_B)$; for some purposes it may be useful to derive such a difference signal, which may be employed to generate a pictorial display in a similar manner to that discussed above for the composite video signal. In cases where there are no significant variations of brightness over the scene viewed by the camera, such a difference signal would of course provide an adequate representation of variations of the degree of polarisation.

Exactly the same principles as just discussed may be applied in the case where the two video signals are generated successively using a single photosensitive screen; in this case the polarisation analysing system may comprise a single linear polariser disposed in front of the screen and having its polarisation direction rotated through 90° between the generation of one video signal and the generation of the other.

Three differential optical polarisation detectors in accordance with the invention will now be described by way of example with reference to the accompanying drawings, in which.

Figure 1:
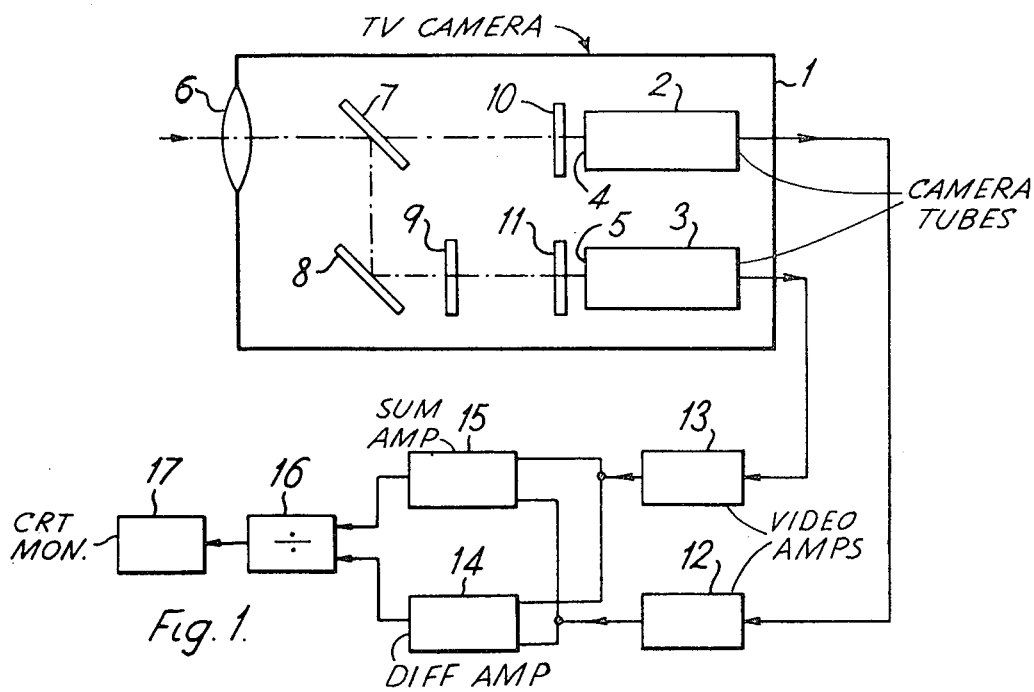
FIG. 1 is a diagrammatic representation of a detector employing a monochrome picture display.

The detector illustrated in FIG. 1 comprises a television camera 1 which includes two similar conventional camera tubes 2 and 3 which are matched as nearly as possible. Light from the scene viewed by the camera 1 is imaged on to the photosensitive screens 4 and 5 of the tubes 2 and 3 by means of an optical system 6 (diagrammatically represented as a single lens); the optical system 6 may be omitted if the detector is to be used with an optical instrument, such as an astronomical telescope or a microscope, having its own image-forming optical system. A beam splitter 7 is disposed in the path of the incident light, the light arriving at the screen 4 being transmitted through the beam splitter 7 and the light arriving at the screen 5 being reflected by the beam splitter 7 and by a mirror 8; a glass compensator 9 is disposed in the path of the reflected beam of light so as to equalise the optical paths for the two beams without affecting the polarisation characteristics of the reflected beam. The camera 1 further incorporates a polarisation analysing system constituted by two linear polarisers 10 and 11 respectively disposed in front of the screens 4 and 5, the polarisers 10 and 11 having their polarising directions set respectively parallel and perpendicular to the plane containing the axes of the transmitted and reflected beams of light (i.e., the plane of the diagram of the camera 1 in FIG. 1); this arrangement ensures the avoidance of any undesirable effects which might occur due to polarisation introduced by the beam splitter 7 and the mirror 8. The beam splitting system is designed so that the screens 4 and 5 would be equally illuminated in the absence of the polarisers 10 and 11.

The tubes 2 and 3 operate in conventional fashion to provide two similar video signals respectively representing the point-by-point variations of intensity in the illumination of the screens 4 and 5, the scanning of the screens 4 and 5 being appropriately synchronised and being in the conventional form of a regular sequence of picture scans each consisting of a large number of parallel lines; the necessary scanning and synchronising systems are of conventional form and for the sake of simplicity they are not shown in the drawing. The two video signals are respectively fed to two similar gamma-correcting video amplifiers 12 and 13; the outputs of the amplifiers 12 and 13 (respectively having instantaneous magnitudes $V_A$ and $V_B$) are fed to the inputs of a unity gain differential amplifier 14 to produce a signal having an instantaneous magnitude $(V_A - V_B)$, and to the inputs of a unity gain summing amplifier 15 to produce a signal having an instantaneous magnitude $(V_A + V_B)$; it will be appreciated that the latter signal represents the spatial variations of brightness in the scene viewed by the camera 1, and it will subsequently be referred to as the brightness signal. The signals produced by the amplifiers 14 and 15 are fed to a dividing unit 16 (for example a four quadrant transconductance divider of high speed capability) to produce a composite video signal having an instantaneous magnitude proportional to $(V_A - V_B)/(V_A + V_B)$; this signal represents the spatial variations of the degree of polarisation of light from the scene viewed by the camera 1, and will subsequently be referred to as the polarisation signal. The polarisation signal is fed to a monitor 17 incorporating a monochrome cathode ray tube, the polarisation signal being utilised in conventional fashion to modulate the electron beam of this tube and the screen of this tube being scanned in synchronism with the scanning of the screens 4 and 5. The monitor 17 thus provides a picture in which brightness variations represent variations in the degree of polarisation of light from the scene viewed by the camera 1. If desired, switching means (not shown) may be provided to permit the difference signal appearing at the output of the differential amplifier 14 to be fed to the monitor 17 instead of the polarisation signal.

Figure 2:
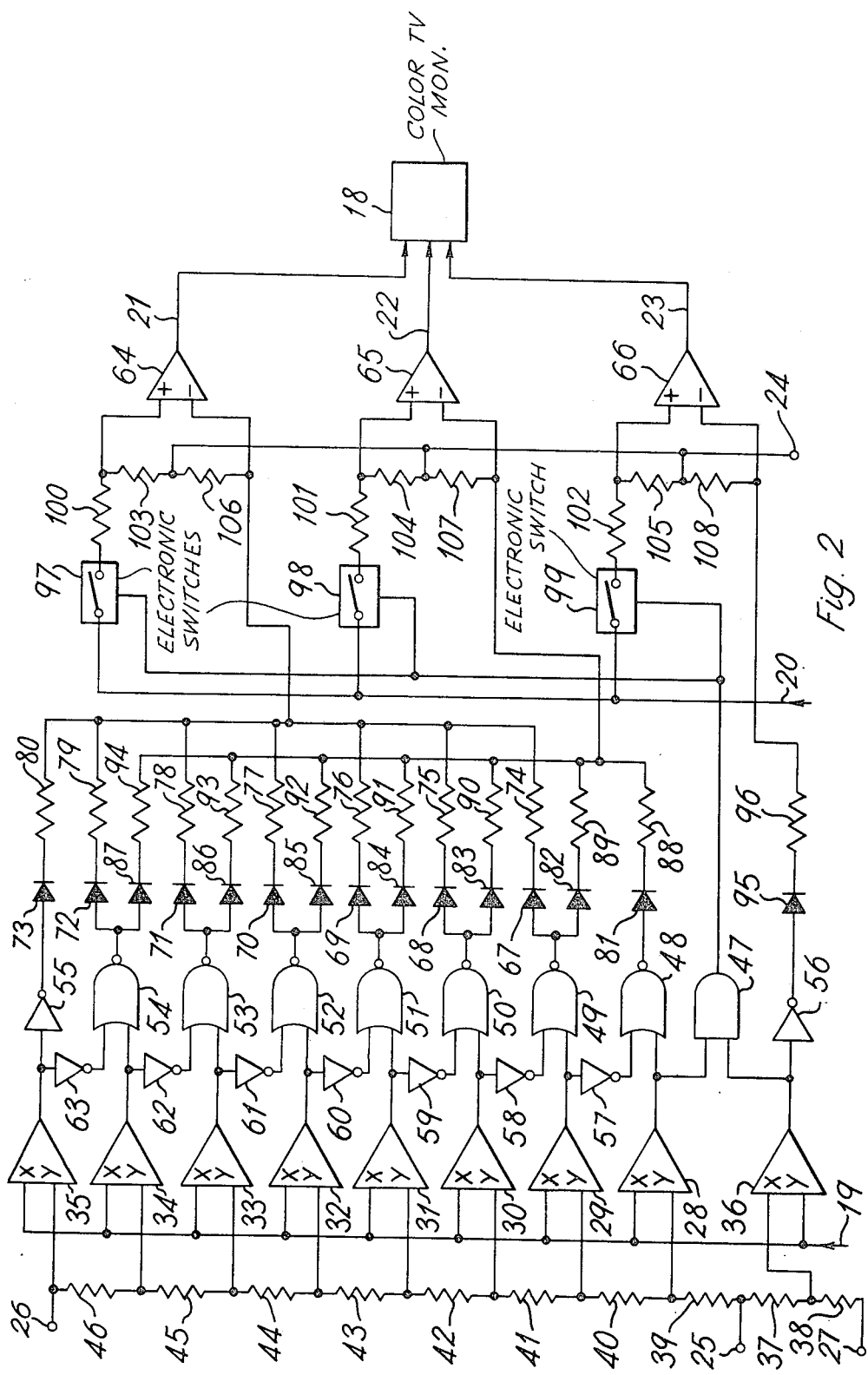
FIG. 2 is a diagram illustrating part of a detector employing a colour picture display.

The second detector to be described incorporates components 1 – 16 identical with those shown in FIG. 1; in this case, however, instead of the polarisation signal being fed to a monitor 17, the polarisation and brightness signals are fed to a colour matrix unit, the details of which are shown in FIG. 2. This unit generates three colour component signals that are fed to a monitor 18 incorporating a colour television tube of the three-gun shadow-mask type, the colour component signals being utilised in conventional fashion to modulate the three electron beams of this tube and the screen of this tube being scanned in synchronism with the scanning of the screens 4 and 5. The colour matrix unit has input lines 19 and 20 to which the polarisation and brightness signals are respectively applied and output lines 21, 22 and 23 on which there appear respectively the "red", "green" and "blue" colour component signals for application to the monitor 18. The unit also has terminals 24, 25, 26, and 27 to which are applied static operating voltages such that the terminals 24 and 25 are held at a nominal zero voltage and the terminals 26 and 27 are respectively held positive and negative. The polarisation signal is applied to the line 19 with a D.C. level and polarity such that zero, positive and negative voltages on the line 19 respectively correspond to zero, positive and negative values of the degree of polarisation; the brightness signal is applied to the line 20 with a D.C. level and polarity such that the black and white levels of this signal respectively correspond to zero and negative voltages on the line 20.

The unit comprises nine high speed binary comparators 28 – 36, each of which has inputs X and Y and is operative so as to provide an output voltage which is zero or positive (logic 0 and 1 states respectively) according to whether or not the input X is more positive than the input Y. The input X of each of the comparators 28 – 35 is connected to the line 19 and the input X of the comparator 36 is connected to the junction between two resistors 37 and 38 connected in series between the terminals 25 and 27; the inputs Y of the comparators 28 – 34 are respectively connected to successive tapping points on a series chain of eight resistors 39 – 46 connected between the terminals 25 and 26, the input Y of the comparator 35 is connected to the terminal 26, and the input Y of the comparator 36 is connected to the line 19. It will be seen that as the value of the polarisation signal varies there are ten possible combinations of the output states of the comparators 28 – 36, viz. one in which the states are all logic 1, one in which the states are logic 1 for the comparators 28 – 35 and lobic 0 for the comparator 36, and eight in which the states are logic 0 respectively for the first one to eight of the comparators 28 – 36 and logic 1 for the remainder. The values of the voltages applied to the terminals 26 and 27 and of the resistors 37 – 46 are chosen so that these combinations respectively correspond to small values (either positive or negative) of the degree of polarisation, substantial negative values of the degree of polarisation, and eight consecutive ranges of substantial positive values of the degree of polarisation.

The outputs of the comparators 28 – 36 are connected to a set of logic elements consisting of an AND gate 47, seven NOR gates 48 – 54 and nine inverters 55 – 63, each of these elements having possible logic 0 and 1 output states similar to those of the comparators 28 – 36. More specifically, the gate 47 has two inputs respectively connected to the outputs of the comparators 28 and 36, the gates 48 – 54 have first inputs respectively connected to the outputs of the comparators 28 – 34 and second inputs respectively connected to the outputs of the inverters 57 – 63, whose inputs are respectively connected to the outputs of the comparators 29 – 35, and the inverters 55 and 56 have their inputs respectively connected to the outputs of the comparators 35 and 36. The arrangement is such that at any given time the output of one, and only one, of the ten elements 47 – 56 is in the logic 1 state, depending on which of the ten possible combinations of the output states of the comparators 28 – 36 exists at that time.

The generation of the colour component signals is effected by applying appropriate signals to three differential amplifiers 64 – 66 whose outputs are respectively connected to the lines 21 – 23, in dependence upon which of the elements 47 – 56 has its output in the logic 1 state. Thus the outputs of the elements 49 – 55 are connected, respectively via diodes 67 – 73 and resistors 74 – 80, to the inverting input of the amplifier 64, the outputs of the gates 48 – 54 are connected, respectively via diodes 81 – 87 and resistors 88 – 94, to the inverting input of the amplifier 65, and the output of the inverter 56 is connected via a diode 95 and a resistor 96 to the inverting input of the amplifier 66. The output of the gate 47 is utilised to control the states of three electronic switches 97 – 99 which are respectively connected in series with resistors 100 – 102 between the line 20 and the respective non-inverting inputs of the amplifiers 64 – 66, the switch 97 – 99 being open when the output of the gate 47 is in the logic 0 state and closed when the output of gate 47 is in the logic 1 state. The input circuits of the amplifiers 64 – 66 are completed by resistors 103 – 105 connected between the terminal 24 and the respective non-inverting inputs of the amplifiers 64 – 66, and resistors 106 – 108 connected between the terminal 24 and the respective inverting inputs of the amplifiers 64 – 66.

The operation of the colour matrix unit is thus as follows. When the polarisation signal has a value corresponding to a substantial negative value of the degree of polarisation, a fixed positive signal will be applied to the inverting input of the amplifier 66, but no other signals will be applied to the amplifiers 64 – 66; the corresponding element of the picture displayed by the monitor 18 will then be coloured blue. When the polarisation signal has a value corresponding to a positive value of the degree of polarisation lying in the lowest of the eight ranges referred to above, a fixed positive signal will be applied to the inverting input of the amplifier 65, but no other signals will be applied to the amplifiers 64 – 66; the corresponding element of the picture displayed by the monitor 18 will then be coloured green. When the polarisation signal has a value corresponding to a positive value of the degree of polarisation lying in the highest of the eight ranges, a fixed positive signal will be applied to the inverting input of the amplifier 64, but no other signals will be applied to the amplifiers 64 – 66; the corresponding element of the picture displayed by the monitor 18 will then be coloured red. When the polarisation signal has a value corresponding to a positive value of the degree of polarisation lying in one of the intermediate six of the eight ranges, fixed positive signals will be applied to the inverting inputs of the amplifiers 64 and 65, but no other signals will be applied to the amplifiers 64 – 66; the corresponding element in the picture displayed by the monitor 18 will then have a hue determined by the relative magnitudes of the signals applied to the amplifiers 64 and 65, and the values of the resistors 74 – 79 and 89 – 94 are chosen so that the six possible hues constitute a graded sequence going from green and red as the value of the degree of polarisation increases. Finally, when the polarisation signal has a value corresponding to a small value (either positive or negative) of the degree of polarisation, no signals will be applied to the inverting inputs of the amplifiers 64 – 66 but negative signals, all proportional to the value of the brightness signal, will be applied to the non-inverting inputs of all the amplifiers 64 – 66; the relative proportions of these signals are appropriately balanced, by choice of the values of the resistors 100 – 105, so that the corresponding element in the picture displayed by the monitor 18 will be achromatic, its brightness of course depending on the value of the brightness signal.

The net result is that the picture displayed by the monitor 18 will provide a colour-coded representation of the spatial variations of degree of polarisation in the light from the scene viewed by the camera 1, negative values of the degree of polarisation being readily distinguishable from positive values and the latter being coded in ranges of magnitude which can be chosen as desired; this colour-coded representation will be effectively superimposed on a background constituted by a conventional monochrome picture of the scene viewed by the camera 1, thus enabling an observer readily to correlate normally visible features in this scene with features shown up by the coloured parts of the picture.

Figure 3:
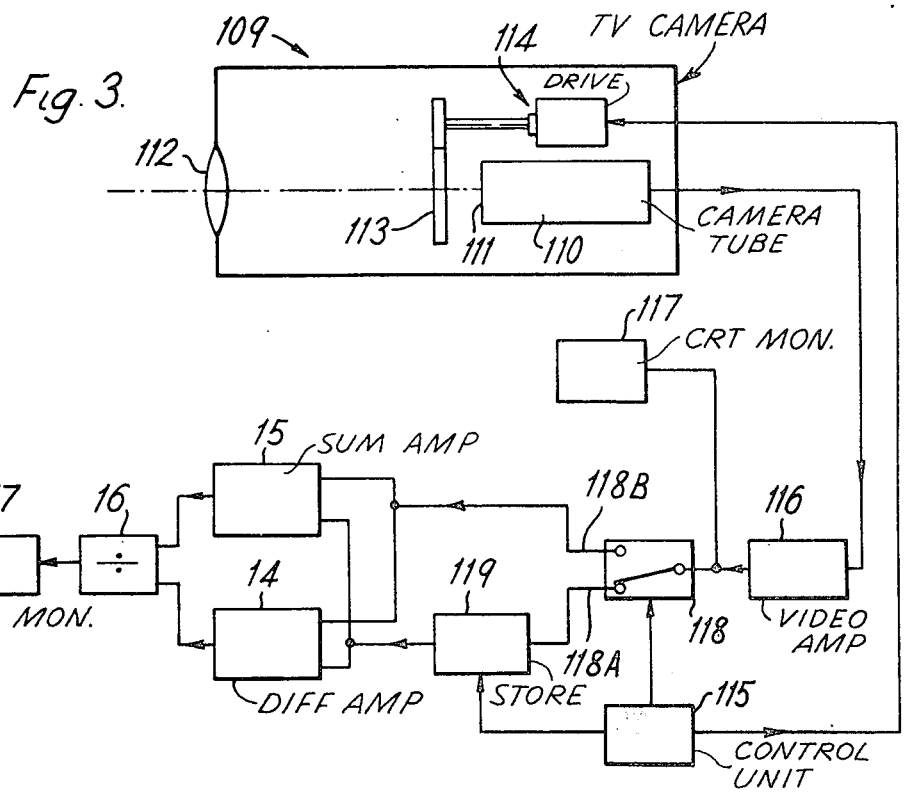
FIG. 3 is a diagrammatic representation of an alternative form of detector employing a monochrome picture display.

The third detector to be described utilises a sequential system instead of the simultaneous system employed in the detectors described above, thereby avoiding any requirement for the close matching of two camera tubes or the provision of a special type of camera tube. Referring to FIG. 3, in this detector the television camera 109 incorporates a single conventional camera tube 110, which again operates in conventional fashion with a conventional form of scanning of its photosensitive screen 111. Light from the scene viewed by the camera 109 is imaged on the screen 111 by an optical system 112, there being disposed in front of the screen 111 a linear polariser 113 whose polarising direction is arranged to be rotatable in steps of 90° by means of a motor drive system 114. The drive system 114 is arranged to be operated during each interval between successive picture scans, under the control of signals derived from a control unit 115 whose operation is synchromised with the scanning of the screen 111; the output of the tube 110 thus alternates at the picture frequency between two video signals respectively representing the required two views of the scene.

The output of the tube 110 is fed to a gamma-correcting video amplifier 116, the output of which is applied to a cathode ray tube monitor 117 for checking for signals. The output of the amplifier 116 is also fed to a two-way switching device 118 (for example a gated amplifier) which is operated in synchronism with the drive system 114 under the control of signals from the unit 115, so that the two video signals appear (in alternate picture periods) respectively at outputs 118A and 118B. The signal appearing at the output 118A is fed to a storage device 119, which operates under the control of signals from the unit 115 so that the stored signal is read out with a delay equal to one picture period; the storage device 119 may for wxample be a cathode ray tube device with "write-in" on one face and "read-out" from the other face of a thin storage film. The delayed signal derived from the storage device 119 and the signal appearing at the output 118B are utilised in a similar manner to the outputs of the amplifiers 12 and 13 in the FIG. 1 arrangement, the detector incorporating components 14 – 17 similar to those shown in FIG. 1. If desired the monitor 17 may again be replaced by an arrangement as shown in FIG. 2 to provide a colour picture display.

It will be appreciated that in the detector illustrated in FIG. 3 the outputs of the components 14, 15 and 16 will have zero values during alternate picture periods. In order to avoid flicker effects it may therefore be desirable to use in this case a higher picture frequency than is the case in conventional television systems.

In the detectors described above provision may be made, if desired, for the insertion of a suitable filter (not shown) in the path of the incident light so as to restrict the wavelength range of the light falling on the screens 4 and 5 or the screen 111. In the FIG. 1 arrangement, the filter should of course be inserted before the beam splitter 7.

We claim:

1. A television system for detecting differential optical polarisation effects, said system comprising:
    a television camera incorporating photosensitive means for generating, in response to illumination by light from the scene viewed by the camera, video signals representing the spatial variations in two dimensions over said scene of the intensity of illumination, and analysing means for causing said photosensitive means to be illuminated separately by linearly polarised parts of the light from said scene which have their respective vibration planes in two orientations at right angles to each other;
    means for deriving separately from said photosensitive means two similar video signals respectively representing two-dimensional pictures of said scene respectively derived by means of two linearly polarised components of the light from said scene which differ only by having their respective vibration planes in said two orientations;
    means for utilising said two video signals to generate a composite video signal representing the spatial variations in two dimensions over said scene of the degree of polarisation given by the ratio of the difference between the intensities of said components to the sum of the intensities of said components;
    display means for displaying a two-dimensional television picture; and
    means for utilising said composite video signal to cause the picture displayed by said display means to provide a representation of said spatial variations of said degree of polarisation.

2. A television system according to claim 1, in which said display means comprises a colour television tube which displays said picture, said means for utilising said composite video signal comprises means for causing said picture to provide a stepwise colour coding of said degree of polarisation and means for causing said picture to contain achromatic elements corresponding to parts of said scene for which said degree of polarisation has a small value; and the television system further comprises means for causing the brightness of said achromatic elements to be dependent on the brightness of the corresponding parts of said scene.

3. A method of detecting differential optical polarisation effects over a scene of defined format, the method comprising:
    generating two similar video signals respectively representing two-dimensional pictures of said scene respectively derived by means of two linearly polarised components of the light from said scene which differ only by having their respective vibration planes at right angles to each other;
    utilising said two video signals to generate a composite video signal representing the spatial variations in two dimensions over said scene of the degree of polarisation given by the ratio of the difference between the intensities of said components to the sum of the intensities of said components; and
    utilising said composite video signal in the generation of a two-dimensional television picture having said defined format to cause said television picture to provide a representation of said spatial variations of said degree of polarisation.

4. A method according to claim 3, in which said composite video signal is utilised to control spatial variations of colour in said television picture to provide a stepwise colour coding of said degree of polarisation and to cause said television picture to contain achromatic elements corresponding to parts of said scene for which said degree of polarisation has a small value, and the brightness of said achromatic components is caused to be dependent on the brightness of the corresponding parts of said scene.

* * * * *